United States Patent
McCurry et al.

(10) Patent No.: US 12,394,572 B2
(45) Date of Patent: Aug. 19, 2025

(54) ELECTROLYTIC CAPACITOR

(71) Applicant: Pacesetter, Inc., Sylmar, CA (US)

(72) Inventors: Troy L. McCurry, West Union, SC (US); R. Jason Hemphill, Sunset, SC (US); Rodrick B. Sauls, Anderson, SC (US)

(73) Assignee: Pacesetter, Inc., Sylmar, CA (US)

( * ) Notice: Subject to any disclaimer, the term of this patent is extended or adjusted under 35 U.S.C. 154(b) by 644 days.

(21) Appl. No.: 17/644,714

(22) Filed: Dec. 16, 2021

(65) Prior Publication Data

US 2022/0310329 A1    Sep. 29, 2022

Related U.S. Application Data

(60) Provisional application No. 63/167,427, filed on Mar. 29, 2021.

(51) Int. Cl.
*A61N 1/00* (2006.01)
*A61N 1/39* (2006.01)
*H01G 9/10* (2006.01)

(52) U.S. Cl.
CPC ............. *H01G 9/10* (2013.01); *A61N 1/3956* (2013.01)

(58) Field of Classification Search
CPC ................................ A61N 1/3956; H01G 9/10
USPC ........................................................... 607/36
See application file for complete search history.

(56) References Cited

U.S. PATENT DOCUMENTS

| | | | | |
|---|---|---|---|---|
| 6,006,133 A | * | 12/1999 | Lessar | A61N 1/3956 361/518 |
| 6,819,544 B1 | * | 11/2004 | Nielsen | H01G 9/10 361/508 |
| 2005/0154423 A1 | * | 7/2005 | Goedeke | A61N 1/3758 607/36 |
| 2008/0170353 A1 | * | 7/2008 | Swanson | H01G 9/08 361/522 |
| 2010/0175235 A1 | * | 7/2010 | Nielsen | H01G 9/08 29/25.03 |
| 2017/0354828 A1 | * | 12/2017 | Bowen | H01G 9/02 |
| 2018/0033561 A1 | * | 2/2018 | McCurry | H01G 9/08 |

* cited by examiner

*Primary Examiner* — Nicole F Johnson
(74) *Attorney, Agent, or Firm* — Dean D. Small; The Small Patent Law Group, LLC

(57) ABSTRACT

A capacitor is provided that includes a capacitor stack including an anode layer, cathode layer, and electrolytic layer electrically coupled together, the capacitor stack including a capacitor stack periphery. The capacitor also includes a first cover portion having a first cover portion periphery that aligns with the capacitor stack periphery, and a second cover portion having a second cover portion periphery that aligns with the capacitor stack periphery and received the first cover portion periphery to form a shell body for encasing the capacitor stack therein. The capacitor stack is isolated from the second cover portion to provide a neutrally charged second cover portion that is electrically coupled within an implanted medical device.

17 Claims, 11 Drawing Sheets

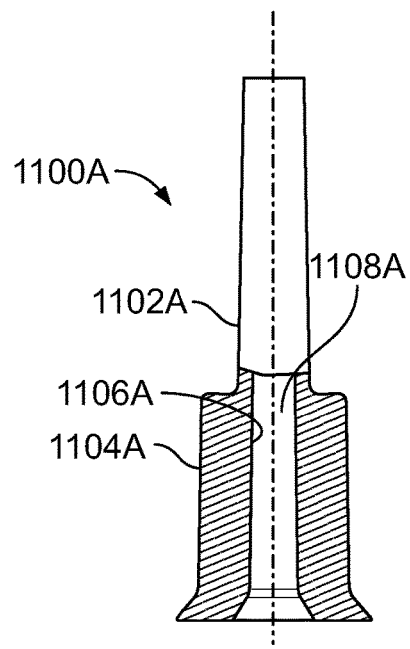
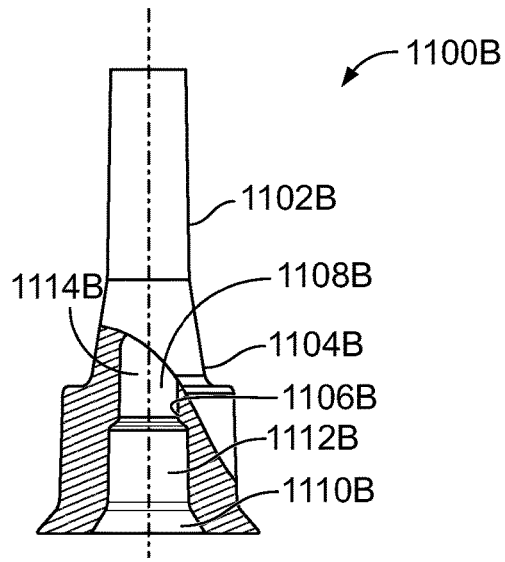
FIG. 11A          FIG. 11B
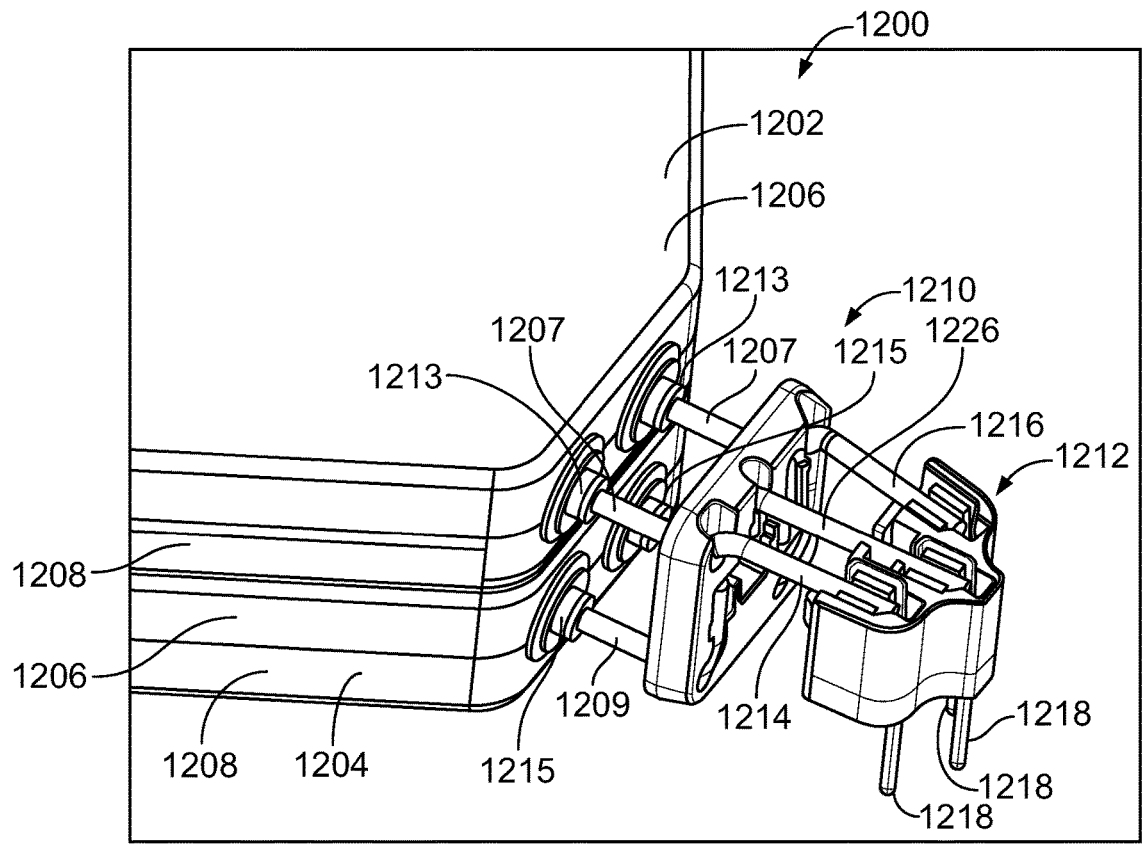
FIG. 12

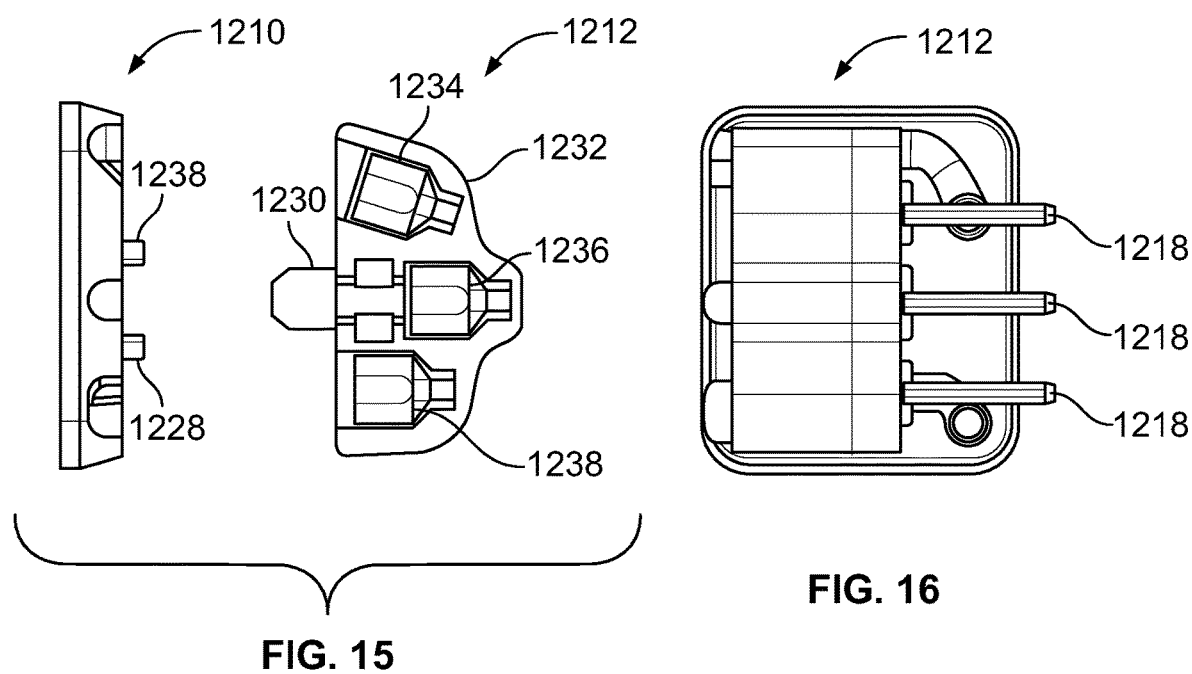

ELECTROLYTIC CAPACITOR

CROSS-REFERENCE TO RELATED APPLICATIONS

This application claims priority benefit to U.S. Provisional Application No. 63/167,427, which was filed on 29 Mar. 2021, and the disclosure of which is incorporated herein by reference in its entirety.

BACKGROUND

Embodiments herein generally relate to electrolytic capacitors utilized for implanted medical devices (IMDs).

High voltage capacitors are utilized as energy storage reservoirs in many applications, including IMDs. These capacitors are required to have a high energy density, to minimize the overall size of the implanted device. Such capacitors may be stacked electrolytic capacitors, typically constructed with a plurality of anodes and cathodes that separated by a liquid-absorbent insulating material that can be referred to as electrolytic paper. The electrolytic paper may be impregnated by an electrically conductive electrolyte.

Improvement of the surface area creation per anode allows for the decrease of final volume of the capacitor to improve energy density through higher efficiency of packaging efficiency. However, the higher packaging efficiency needs to maintain lower tolerances on case/lid configurations, boot geometries, and several design rule electrical standoff tolerances. The lower tolerances lead to higher cost for bill of materials (BOM) choices, lower reliability, and lower yield. Often thin pockets of poly(ether ether ketone) (PEEK) must be utilized for protection of the stacked electrolytic capacitor. Such protection requires precise manufacturing techniques, including complex manufacturing processes.

In addition, the lower tolerances and thin PEEK pockets can lead to the capacitor being prone to cracking, decreasing the life of the capacitor. In addition, the out connection of the capacitor is a negative output resulting in decreased internal resistance within the capacitor that can result in increased capacitor temperatures, bubbling, and even failure.

Further, for IMD application, because the IMD is subcutaneous, or under the skin of the patient, the size of the IMD must remain minimal. Meanwhile, the capacitor can represent the largest electrical component within the IMD. As a result, manufacturing constraints are also presented, preventing increases in tolerances or spatial changes to address cracking issues, internal capacitor resistances resulting in heat build-up and deformation, manufacturing complexities, or the like.

SUMMARY

In accordance with embodiments herein, a capacitor is provided that includes a capacitor stack including an anode layer, cathode layer, and electrolytic layer electrically coupled together, the capacitor stack including a capacitor stack periphery. The capacitor also includes a first cover portion having a first cover portion periphery that aligns with the capacitor stack periphery, and a second cover portion having a second cover portion periphery that aligns with the capacitor stack periphery and received the first cover portion periphery to form a shell body for encasing the capacitor stack therein. The capacitor stack is isolated from the second cover portion to provide a neutrally charged second cover portion that is electrically coupled within an implanted medical device.

Optionally, the first cover portion comprises an injection molded plastic. In one aspect the second cover portion is a metal case. In one aspect, the second cover portion comprises stainless steel. In another aspect, the capacitor stack includes an anode coupled to a first ferrule that extends through the shell body, and a cathode coupled to a second ferrule that extends through the shell body. In one example, the cathode includes a flat that that is welded to a wire assembly.

In one embodiment, the capacitor stack periphery includes a front that arcuately transitions to an input side that includes a first portion and a second portion angled from the first portion, the input side arcuately transitions to a back that arcuately transitions into an arcuate side that arcuately transitions into the front. In another embodiment, the first cover periphery includes a front that arcuately transitions to an input side that includes a first portion and a second portion angled from the first portion, the input side arcuately transitions to a back that arcuately transitions into an arcuate side that arcuately transitions into the front of the first cover periphery, and the second cover periphery includes a front that arcuately transitions to an input side that includes a first portion and a second portion angled from the first portion, the input side arcuately transitions to a back that arcuately transitions into an arcuate side that arcuately transitions into the front of the second cover periphery.

In accordance with embodiments herein, a method for manufacturing a capacitor for an implanted medical device is provided that includes forming a capacitor stack including an anode layer, cathode layer, and electrolytic layer that has a capacitor stack periphery. The method also includes forming a first cover portion having a first cover portion periphery that aligns with the capacitor stack periphery, and forming a second cover portion having a second cover portion periphery that aligns with the capacitor stack periphery. The method also includes disposing the capacitor stack within the first cover portion and second cover portion, forming an anode and cathode in the capacitor stack coupling a first ferrule to the cathode, and coupling a second ferrule to the anode.

Optionally, forming the first cover portion comprises injection molding a plastic material to form a boot. In one aspect, forming the second cover portion comprises stamping metal to form a case. In one example, the method also includes welding a wire assembly to a flat of the cathode. In another example, the method also includes adhering adhesive tape to the capacitor stack periphery. In one embodiment, the method additionally includes sealing an opening disposed through the first cover portion, and/or second cover portion with a ball element.

In accordance with embodiments herein, a capacitor assembly is provided that includes a first capacitor having a first capacitor stack including an anode layer, cathode layer, and electrolytic layer electrically coupled together, the first capacitor stack including a first capacitor stack periphery. The first capacitor also includes a first shell body having a first cover portion with a first cover portion periphery that aligns with the first capacitor stack periphery, and a second cover portion having a second cover portion periphery that aligns with the first capacitor stack periphery and receives the first cover portion periphery for encasing the first capacitor stack therein. The capacitor assembly also includes a second capacitor that has a second capacitor stack including an anode layer, cathode layer, and electrolytic layer electrically coupled together, the second capacitor stack including a second capacitor stack periphery. The second capacitor also includes a second shell body stacked on the first shell body and has a first cover portion with a first cover portion periphery that aligns with the second capacitor stack periphery, and a second cover portion having a second cover portion periphery that aligns with the second capacitor stack periphery and received the first cover portion periphery for encasing the second capacitor stack therein. The capacitor assembly also includes a backing plate mechanically coupled to the first shell body and the second shell body and electrically coupled to an electronic coupler to provide an anode input and cathode input.

Optionally, the electronic coupler includes at least one pin element. In one aspect, the second cover portion of the first shell body is neutrally charged, and the second cover portion of the second shell body is neutrally charged. In another aspect, the backing plate receives a first ferrule and second ferrule extending from the first shell body, and the backing plate receives a first ferrule and second ferrule extending from the second shell body. In one example, the first shell body has a first size and shape, and the second shell body has a second size and shape. The first size and shape are identical to the second size and shape. In yet another example, the electronic coupler is electrically coupled within an implanted medical device.

DESCRIPTION OF THE DRAWINGS

FIG. 11A illustrates a sectional view of an injection device, in accordance with embodiments herein.

FIG. 11B illustrates a sectional view of an injection device, in accordance with embodiments herein.

FIG. 12 illustrates a perspective view of a capacitor assembly, in accordance with embodiments herein.

FIG. 15 illustrates a plan view of a backing plate and electronic coupler, in accordance with embodiments herein.

FIG. 16 illustrates a plan view of a backing plate and electronic coupler, in accordance with embodiments herein.

DETAILED DESCRIPTION

Figure 1:
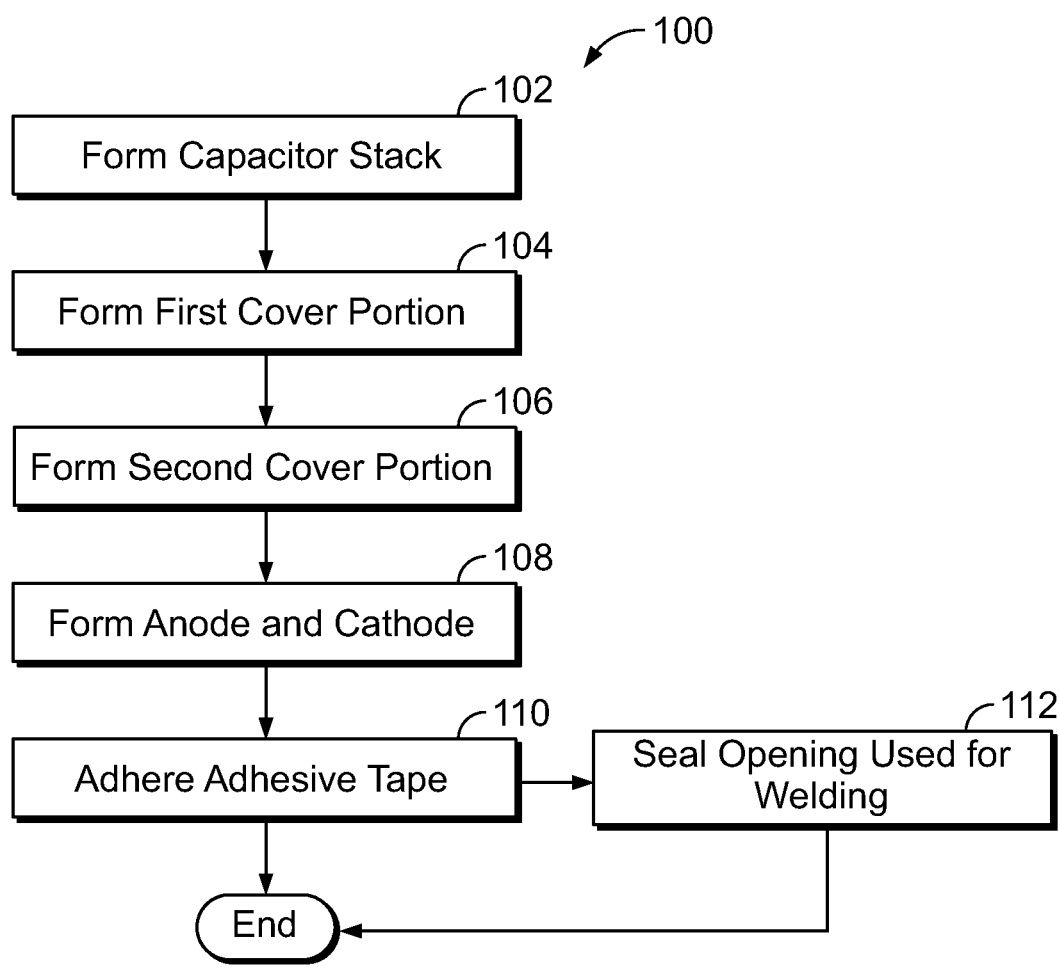
FIG. 1 illustrates a flow block diagram of a method for manufacturing a capacitor, in accordance with embodiments herein.

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein.

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

All references, including publications, patent applications and patents, cited herein are hereby incorporated by reference to the same extent as if each reference were individually and specifically indicated to be incorporated by reference and were set forth in its entirety herein.

Terms

The term "capacitor stack" refers to a group of layers placed one on top of another to provide an electrical output for a capacitor. A capacitor stack can include at least one anode layer, at least one cathode layer, and at least one electrolytic layer. Though in some embodiments plural anode layers, plural cathode layers, and plural electrolytic layers are provided. Each layer forms a portion of the thickness of the capacitor stack, where the total thickness of the capacitor stack is the combination of the thicknesses of the layers. In one example, the electric output can be an anode or a cathode, where the anode and/or cathode can be welded together and have a thickness that is less than the rest of the capacitor stack.

The term "isolated" refers to two electrical components that do not pass electrical properties or characteristics to and from one another. Such isolation may be a physical isolation such that the two electrical components do not engage one another. In another example, an electrical polarity, is not passed even though engagement of the two electrical components may be presented. As an example, a capacitor stack is considered isolated from a case or cover portion when the negative electrical polarity of the anode is not passed, conducted, or the like to or from the case or covering such that the case or cover portion remains neutral.

The term "ferrule" refers to a tube, such as a metal tube, that is coupled onto the end of a wire. In one example, a soft metal tube is crimped onto the end of a stranded wire to improve the connection characteristics of the wire. In addition, the tube also facilitates the passing of the wire through openings, allowing wires to be feed through the opening during manufacturing.

The term "obtains" and "obtaining", as used in connection with data, signals, information, and the like, include at least one of i) accessing memory of an external device or remote server where the data, signals, information, etc. are stored, ii) receiving the data, signals, information, etc. over a wireless communications link between the IMD and a local external device, and/or iii) receiving the data, signals, information, etc. at a remote server over a network connection. The obtaining operation, when from the perspective of an IMD, may include sensing new signals in real time, and/or accessing memory to read stored data, signals, information, etc. from memory within the IMD. The obtaining operation, when from the perspective of a local external device, includes receiving the data, signals, information, etc. at a transceiver of the local external device where the data, signals, information, etc. are transmitted from an IMD and/or a remote server. The obtaining operation may be from the perspective of a remote server, such as when receiving the data, signals, information, etc. at a network interface from a local external device and/or directly from an IMD. The remote server may also obtain the data, signals, information, etc. from local memory and/or from other memory, such as within a cloud storage environment and/or from the memory of a workstation or clinician external programmer.

Embodiments may be implemented in connection with one or more implantable medical devices (IMDs). Non-limiting examples of IMDs include one or more neurostimulator devices, implantable cardiac monitoring and/or therapy devices. For example, the IMD may represent a cardiac monitoring device, pacemaker, cardioverter, cardiac rhythm management device, implantable cardioverter defibrillator (ICD), neurostimulator, leadless monitoring device, leadless pacemaker, an external shocking device (e.g., an external wearable defibrillator), and the like. For example, the IMD may be a subcutaneous IMD that includes one or more structural and/or functional aspects of the device(s) described in U.S. application Ser. No. 15/973,195, titled "Subcutaneous Implantation Medical Device With Multiple Parasternal-Anterior Electrodes" and filed May 7, 2018; U.S. application Ser. No. 15/973,219, titled "Implantable Medical Systems And Methods Including Pulse Generators And Leads" filed May 7, 2018; U.S. application Ser. No. 15/973,249, titled "Single Site Implantation Methods For Medical Devices Having Multiple Leads", filed May 7, 2018, which are hereby incorporated by reference in their entireties. Additionally or alternatively, the IMD may include one or more structural and/or functional aspects of the device(s) described in U.S. Pat. No. 9,333,351 "Neurostimulation Method and System to Treat Apnea" and U.S. Pat. No. 9,044,710 "System and Methods for Providing A Distributed Virtual Stimulation Cathode for Use with an Implantable Neurostimulation System", which are hereby incorporated by reference. Further, one or more combinations of IMDs may be utilized from the above incorporated patents and applications in accordance with embodiments herein.

Additionally or alternatively, the IMD may include one or more structural and/or functional aspects of the device(s) described in U.S. Pat. No. 9,216,285 "Leadless Implantable Medical Device Having Removable and Fixed Components" and U.S. Pat. No. 8,831,747 "Leadless Neurostimulation Device and Method Including the Same", which are hereby incorporated by reference. Additionally or alternatively, the IMD may include one or more structural and/or functional aspects of the device(s) described in U.S. Pat. No. 8,391,980 "Method and System for Identifying a Potential Lead Failure in an Implantable Medical Device", U.S. Pat. No. 9,232,485 "System and Method for Selectively Communicating with an Implantable Medical Device", EP Application No. 0070404 "Defibrillator" and, U.S. Pat. No. 5,334,045 "Universal Cable Connector for Temporarily Connecting Implantable Leads and Implantable Medical Devices with a Non-Implantable System Analyzer", U.S. patent application Ser. No. 15/973,126, titled "Method And System For Second Pass Confirmation Of Detected Cardiac Arrhythmic Patterns"; U.S. patent application Ser. No. 15/973,351, Titled "Method And System To Detect R-Waves In Cardiac Arrhythmic Patterns"; U.S. patent application Ser. No. 15/973,307, titled "Method And System To Detect Post Ventricular Contractions In Cardiac Arrhythmic Patterns"; and U.S. patent application Ser. No. 16/399,813, titled "Method And System To Detect Noise In Cardiac Arrhythmic Patterns" which are hereby incorporated by reference.

Additionally or alternatively, the IMD may be a leadless cardiac monitor (ICM) that includes one or more structural and/or functional aspects of the device(s) described in U.S. patent application Ser. No. 15/084,373, filed Mar. 29, 2016, entitled, "Method and System to Discriminate Rhythm Patterns in Cardiac Activity"; U.S. patent application Ser. No. 15/973,126, titled "Method And System For Second Pass Confirmation Of Detected Cardiac Arrhythmic Patterns"; U.S. patent application Ser. No. 15/973,351, titled "Method And System To Detect R-Waves In Cardiac Arrhythmic Patterns"; U.S. patent application Ser. No. 15/973,307, titled "Method And System To Detect Post Ventricular Contractions In Cardiac Arrhythmic Patterns"; and U.S. patent application Ser. No. 16/399,813, titled "Method And System To Detect Noise In Cardiac Arrhythmic Patterns", which are expressly incorporated herein by reference.

Provided is an electrolytic capacitor having an anode that has a surface area of 30-40 million tunnels/cm^2 after an etching manufacturing technique as a result of utilizing molybdic acid to provide galvanic aluminum dissociation in a low pH etch solution before the electrochemical process is implemented to increase initiation sites before etching. After etching, an electrochemical widening step is used to increase the tunnel diameter to ensure the formation oxide will not close off the tunnels. As a result, the energy density of the anode is increased by as much as 10%, allowing a smaller, less voluminous anode, and consequently capacitor. Still, in applications such as IMDs, while decreasing the overall size can be beneficial, in addition, by keeping the same size of IMD, benefits can also be realized. In particular, IMDs are sized to be acceptable for a patient using the IMD, so by decreasing the size of the anode and thus capacitor internally within the IMD without decreasing the overall size of the IMD, manufacturing and packaging improvements are provided to reduce BOM costs, reduce manufacturing complexity, and provide additional protections not realized without the molybdic acid manufacturing technique.

FIG. 1 illustrates a method 100 for manufacturing a capacitor. In one example, the capacitor is a high voltage capacitor that can have an operating voltage of between 350-475 Volts and specifically between 400-465 Volts. In one example, the capacitor is utilized in an IMD, including in an implantable cardioverter defibrillator (ICD).

At 102, a capacitor stack is formed that includes at least one anode layer, at least one cathode layer, and at least one electrolytic layer that is disposed between an anode layer and a cathode layer. The anode layer has a surface area of at least 40 million tunnels/cm2. In one example, in order to achieve this surface area, the anode is formed utilizing molybdic acid that allows for galvanic aluminum dissociation in a low pH etch solution before etching occurs. As a result, initiation sites are increased resulting in a capacitance increase compared to other etching techniques.

Because of the increase in energy density of the anode resulting from the increased surface area achieved using the molybdic acid, the anode layer, cathode layer, and electrolytic layer are each sized and shaped to facilitate manufacturing. In particular, when the capacitor is utilized in an IMD, strict spatial requirements are presented. Because of the spatial requirements, when using other etching techniques that do not achieve the surface area presented by use of the molybdic acid, the anode layer must be utilized completely for surface area and functional purposes. With the increase in surface area realized by utilizing the molybdic acid etching technique, the reduced size of the anode layer, and consequently, the cathode layer and electrolytic layer may be utilized to enhance manufacturing capabilities.

In one example, the anode layer, cathode layer, and electrolytic layer can be designed to have peripheries with straight and angled edges, along with increased radii at transitions between the edges. By having a capacitor stack periphery with simple geometries, manufacturing of the capacitor stack is simplified, leading to automation, while decreasing cracking in individual layers as a result to inconsistent geometries. In one example, manual taping of the capacitor stack is not required, and the process of forming the capacitor stack is completely automated. To this end, while adhesive tape may be utilized to bundle the capacitor stack, or to cover seams between layers, because of the simplified, repeatable geometry of the capacitor stack periphery, such adhesive tape may be automatically applied. Alternatively, the amount of time for manual placement of the adhesive tape is reduced.

At 104, a first cover portion is formed. In one example, the first cover portion is formed through an injection molding process, and specifically in one embodiment a plastic injection molding process. As such, the first cover portion comprises an injection molded plastic. In this manner, the first cover portion functions as a plastic boot that encases a portion of the capacitor stack. As used herein, the term boot refers to a covering, that has an open end for receiving a capacitor stack. The covering can be plastic, metal, ceramic, etc., although the covering typically is a plastic injection molded cover portion.

In one example, ferrules that are to be coupled to an anode and cathode of the capacitor stack can be positioned during the injection molding process to ensure an appropriate mechanical and electrical coupling to the anode and cathode. By using a manufacturing process such as injection molding, the formation of the first cover portion can be automated, and repeatable such that the exact same first cover portion can be formed from the same mold. This also allows for replacement of such a first cover portion as needed, and increases the speed of manufacturing time.

At 106, a second cover portion is formed. In one example, the second cover portion is made from a progressive die manufacturing method to form a metal case. The progressive die manufacturing process can include continuously feeding metallic material into a device for stamping, punching, coining, bending, or the like into the geometry and shape presented by the die. After formation, the second cover portion (e.g. metal case) is then ejected for coupling with the first cover portion (e.g. plastic boot). Consequently, as a result of the simplified geometry of the capacitor stack, a matching first cover portion and second cover portion, each with a simplified geometry can be formed using an automated process such an injection molding, progressive die manufacturing, or the like. Therefore, manufacturing is simplified, and more capacitors may be manufactured in a determined period of time than compared to current manufacturing processes.

At 108, an anode and cathode are formed. In one example, the anode is formed by welding the anode layers together at an anode periphery of the anode layers. Similarly, in one example, the cathode if formed by welding cathode layers together at the cathode periphery of cathode layers adjacent the anode. In one example, the cathode includes a titanium cathode flat that is welded to an aluminum wire assembly. A ferrule of the aluminum wire assembly, and a ferrule coupled to the anode can then be feed through a sealing element that guides each ferrule through openings within the first cover portion and/or second cover portion. The sealing elements function to prevent the ferrules from engaging the first cover portion and/or second cover portion and sealing the capacitor stack from the exterior environment. In this manner, the anode is isolated from the second cover portion (e.g. metal case) to provide a neutral output. An anode and cathode wire seal may be provided that does not have a parting line in the sealing surface, resulting in higher reliability of the sealing surface to decrease electrolyte leaks during manufacturing and use.

At 110, an adhesive tape is adhered around the capacitor stack periphery for coupling with the first cover portion and/or the second cover portion. In one example, the tape includes a stainless steel backing band with adhesive that couples to either the first cover portion, and/or the second cover portion. The adhesive tape functions to seal the capacitor stack, and prevent leakage from the electrolytic layers. Additionally, because of the simple geometries of the capacitor stack periphery, the adhesive tape can be automatically applied about the capacitor stack.

At 112, optionally, an opening that is disposed through the first cover portion, and/or second cover portion, and utilized for welding can be sealed. In particular, an opening may be formed in either the first cover portion or second cover portion to access the anode, cathode, capacitor stack, etc. for the purposes of welding therein. In one example, a ball seal is provided within an insert in order to seal the cavity formed by the coupling of the first cover portion and the second cover portion. As such, a sealed cavity is presented.

As provided, because of the decrease in size of the anode, due to the increase in surface area of the anode from using the molybdic acid etching technique, the capacitor stack periphery may be formed with simple geometries and then disposed with a shell body formed from a first cover portion and second cover portion. Such simple geometries permit the first cover portion and second cover portion to be formed using automated, repeatable manufacturing processes, improves protections, and reduces overall cost of the capacitor. To this end, the capacitor can also be reduced in size depending on the voltage requirements of the capacitor.

FIGS. 2-7 illustrate views of a capacitor 200. In one example, the capacitor 200 is formed utilizing the method of FIG. 1. In particular, the capacitor is a high voltage capacitor that can have an operating voltage of between 350-475 Volts and specifically between 400-465 Volts. In one example, the capacitor 200 is utilized in an IMD, including in an implantable cardioverter defibrillator (ICD).

The capacitor 200 includes a capacitor stack 202 that is protected, and covered by a shell body 204 (FIG. 4) that includes a first cover portion 206 and a second cover portion 208 that mechanically couple to one another and define a cavity 210 that receives a capacitor stack 202. In one example, the first cover portion 206 may be made of a plastic material, and represent a plastic boot, while the second cover portion 208 is made of a stainless steel material that functions to protect the capacitor stack 202. While in one example the first cover portion 206 and second cover portion 208 can be of similar size such as when forming the shell body 204, in other example embodiments, the second cover portion 208 may be slightly larger than the first cover portion 206 such that the first cover portion 206 can be received by the second cover portion 208

The capacitor stack 202 includes plural anode layers 212 and cathode layers 214 stacked one on top of another with an electrolytic layer 216 disposed between each anode layer 212 and cathode layer 214. The anode layer 212 is formed utilizing an etching manufacturing technique utilizing molybdic acid to provide galvanic aluminum dissociation in a low pH etch solution. Consequently, the anode has a surface area of 30-40 million tunnels/cm^2 including an increase in tunnel diameter to ensure the formation oxide does not close the tunnels. As a result, the energy density of the anode is increased. The electrolytic layer 216, or paper, include electrolytes allowing the capacitor to hold a charge therein.

Plural sections of adhesive tape 217 hold the multi-layers of the capacitor stack 202 together. In one example, the adhesive tape 217 is a metal tape such as stainless steel. In another example, the tape can be a PEEK tape, or include a layer of PEEK tape. In particular, PEEK tape does not break down under increased temperatures, resulting in increased life of the capacitor. In other examples, another corrosive resistant material can be utilized.

The capacitor stack 202 also includes first and second alignment slots 218, 220 provide an opening for a fastener to secure the first cover portion 206 and second cover portion 208, and also aligns the anode layers 212, cathode layers 214, with the electrolytic layers 216. In one example, the first and second alignment slots 218 and 220 are generally arcuate in shape. In particular, the first alignment slots align the cathode layers 214 and electrolytic layers 216, while the second alignment slots align the anode layers 212 and electrolytic layers 216. Because of etching manufacturing technique utilizing molybdic acid, the first and second alignment slots 218, 220 may be made for alignment and fastening functionality, while the capacitor stack still functions as a high voltage capacitor as a result of the increased energy density of the anode. Similarly, the capacitor stack periphery 221 may have a more pronounced radii or curvature, allowing the shell body 204 to have a simple design. To this end, the capacitor stack 202 has a capacitor stack periphery 221 that includes simple geometries such as straight edges, angled straight edges, arcuate transitions with pronounced radii or curvature, etc. Specifically, in one embodiment, the periphery of the anode layer(s), the periphery of the cathode layer(s), and the periphery of the electrolytic layer(s) all align to form the capacitor stack periphery with the simplified geometries.

The capacitor stack 202 also has a compressed anode portion 222 and compressed cathode portion 224 that present the input and output of the capacitor. The compressed anode portion 222 and compressed cathode portion 224 in one example are each welded together at an end of the capacitor stack 202 such that neither the compressed anode portion 222, nor the compressed cathode portion 224 engage the shell body 204. In particular, when described as compressed, does not indicate that an individual anode layer or cathode layer are compressed, instead, the term compressed is indicating the width of the compressed anode portion 222 and compressed cathode portion 224 is less than the width of the rest of the combined anode layers 212 and combined cathode layers 214. Specifically, by having the compressed anode portion 222 and compressed cathode portion 224 be a smaller width, and not engaging either the first cover portion 206 or second cover portion 208 of the shell body 204, the capacitor remains neutral, instead of having a negative charge. Consequently, additional electronic components are not needed to covert a negatively charged output to a neutral output. Instead by effectively utilizing the spatial arrangement of the capacitor stack 202, such a neutral output is accomplished.

Figure 2:
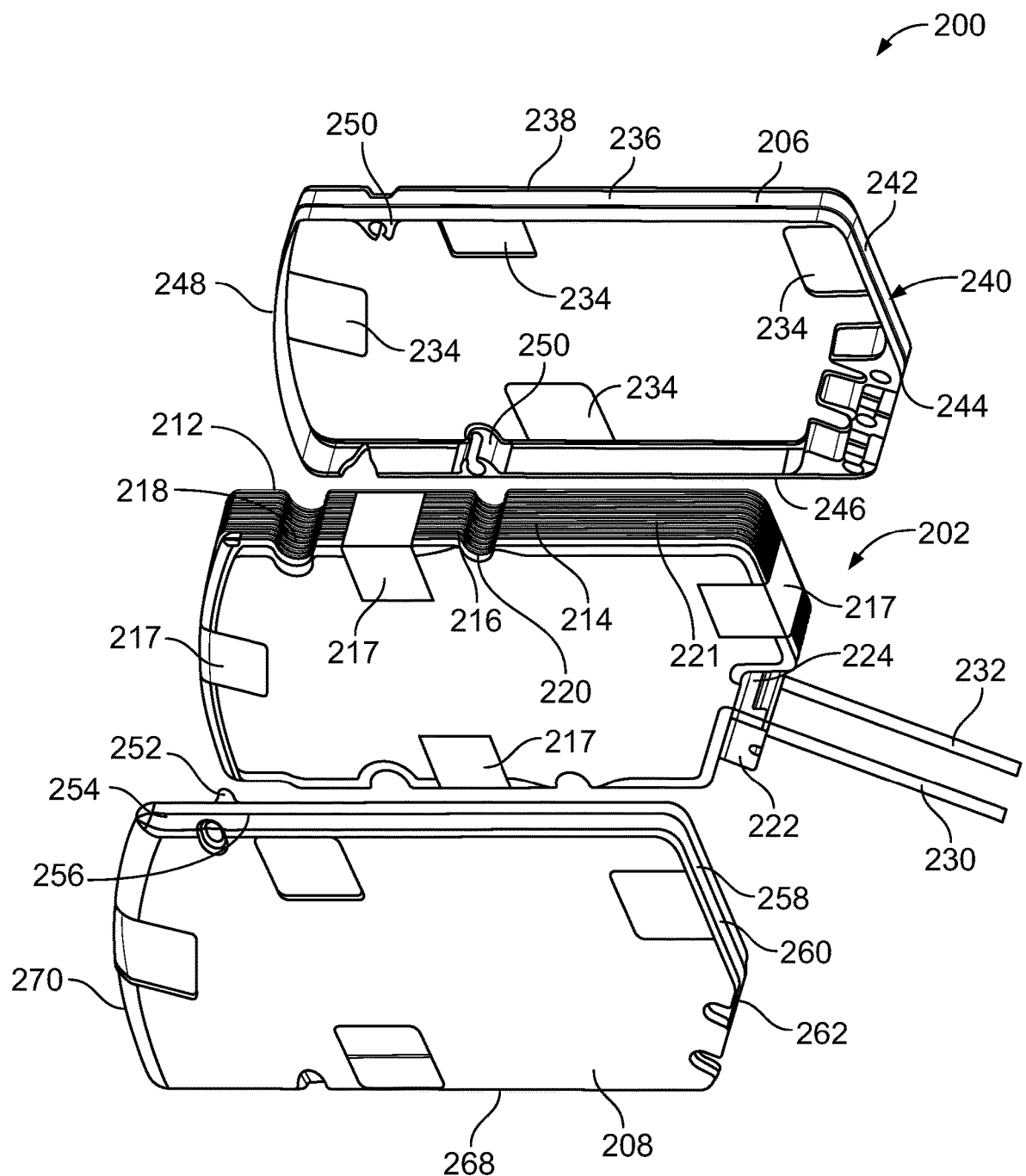
FIG. 2 illustrates an exploded perspective view of a capacitor, in accordance with embodiments herein.

As best illustrated in FIG. 2, the capacitor stack 202 additionally includes a first ferrule support structure 226, and second ferrule support structure 228. The first ferrule support structure 226 supports a first ferrule 230 that couples to the compressed anode portion 222, while the second ferrule support structure 228 supports a second ferrule 232 that couples to the compressed cathode portion 224. In one example, the first and second ferrules 230, 232 each include an insulated material such as rubber to frictionally engage each ferrule 230, 232. The first and second ferrule support structures 226, 228 prevent the first and second ferrules 230, 232 from engaging the first cover portion 206 or second cover portion 208 of the shell body 204, again allowing for a neutral output from the capacitor 200. In addition, the first ferrule support structure 226 and second ferrule support structure 228 have simple geometries, making reproduction of each facilitated. In addition, because the first cover portion 206 can be injection molded as a boot, the ferrules 230, 232 are positioned for feed through from openings 233 (FIG. 3) in the clam shell body 204. In addition, edge taping is eliminated, again eliminating manual labor, decreasing costs, and increasing automation ability. As an additional advantage, the capacitor stack 202 is isolated from the second cover portion 208 to provide a neutrally charged second cover portion 208. As a result, when the capacitor 200 is within an implanted medical device, the second cover portion 208 is neutrally charged, requiring no additional circuitry to vary a negative output, eliminating electronic components of the capacitor 200.

The first cover portion 206 includes plural recesses 234 that align with the adhesive tape 217 that holds the multi-layers of the capacitor stack 202 together. In one example, the first cover portion 206 is considered an exoskeleton of the capacitor. The first cover portion 206 has a first cover portion periphery 236 that includes a front 238 that arcuately transitions to an input side 240 that includes a first portion 242 and a second portion 244 angled from the first portion 242, and having an opening therein configured to receive ferrules of the capacitor stack. The input side 240 only has the simple geometry of the first portion 242 angled to the second portion 244 with no complex geometries. To this end, the input side 240 also arcuately transitions to a back 246 of the first cover portion periphery 236. The arcuate transition between the front 238 and input side 240, along with the arcuate transition between the input side 240 and back 246 have radii that again provide simple geometries. The back 246 extends to another arcuate transition to an arcuate side 248. The arcuate side 248 is generally arcuate, curving to another arcuate transition with the front 238. The first cover portion 206 along the front 238, back 246, input side 240, or arcuate side 248 may include fastener bodies 250 that are of size and shape to accommodate the capacitor stack, and receive fasteners to couple to the second cover portion 208, and secure the first cover portion 206 to the second cover portion 208 with the capacitor stack 202 disposed therein. The fastener bodies 250 may include cavities, indentations, openings, or the like to accommodate the coupling of the first cover portion 206 and second cover portion 208.

Figure 5:
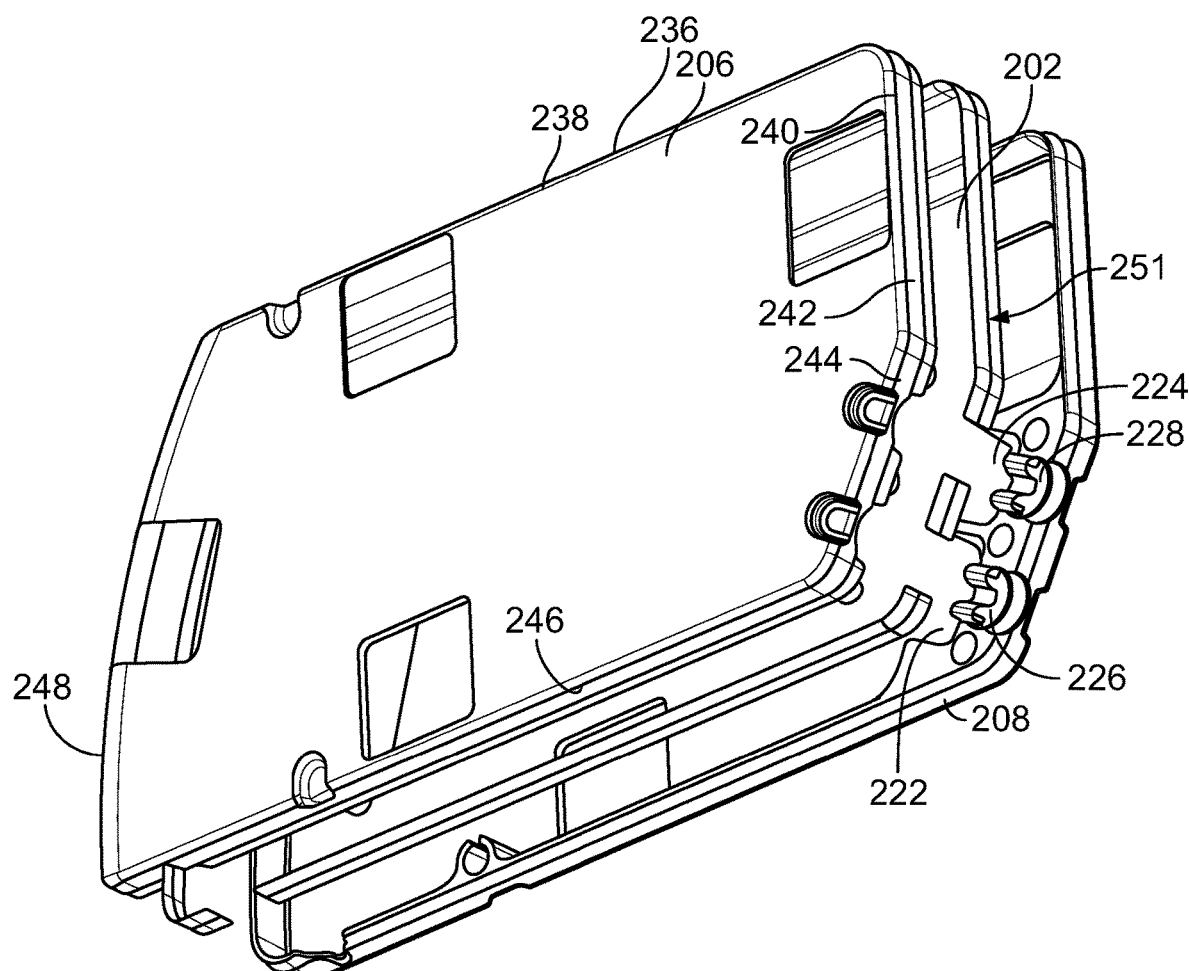
FIG. 5 illustrates an exploded perspective view of a capacitor, in accordance with embodiments herein.
Figure 6:
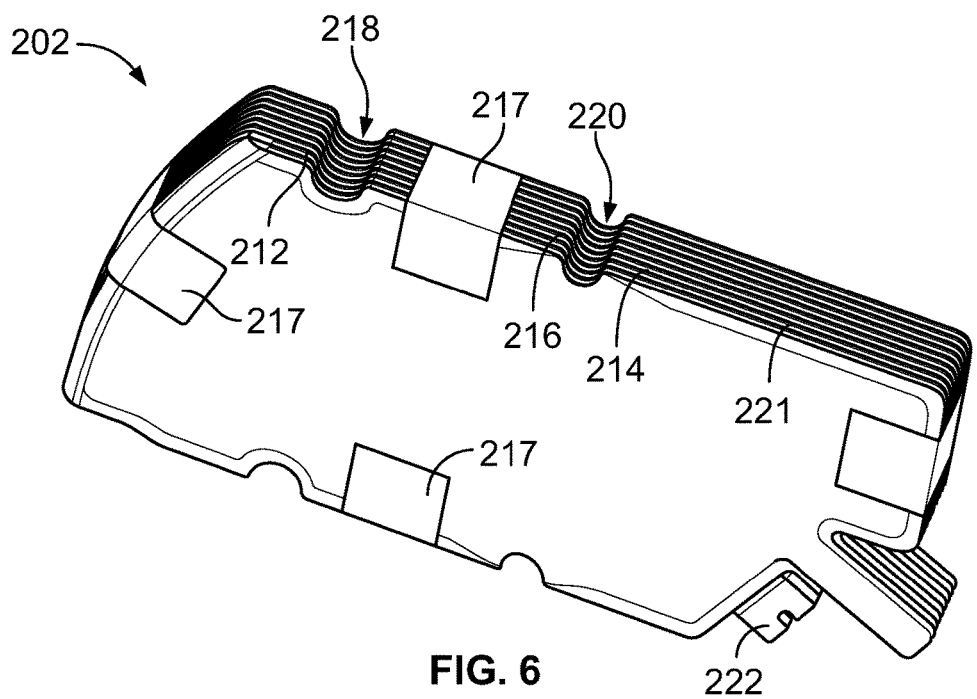
FIG. 6 illustrates a perspective view of a capacitor stack, in accordance with embodiments herein.
Figure 7:
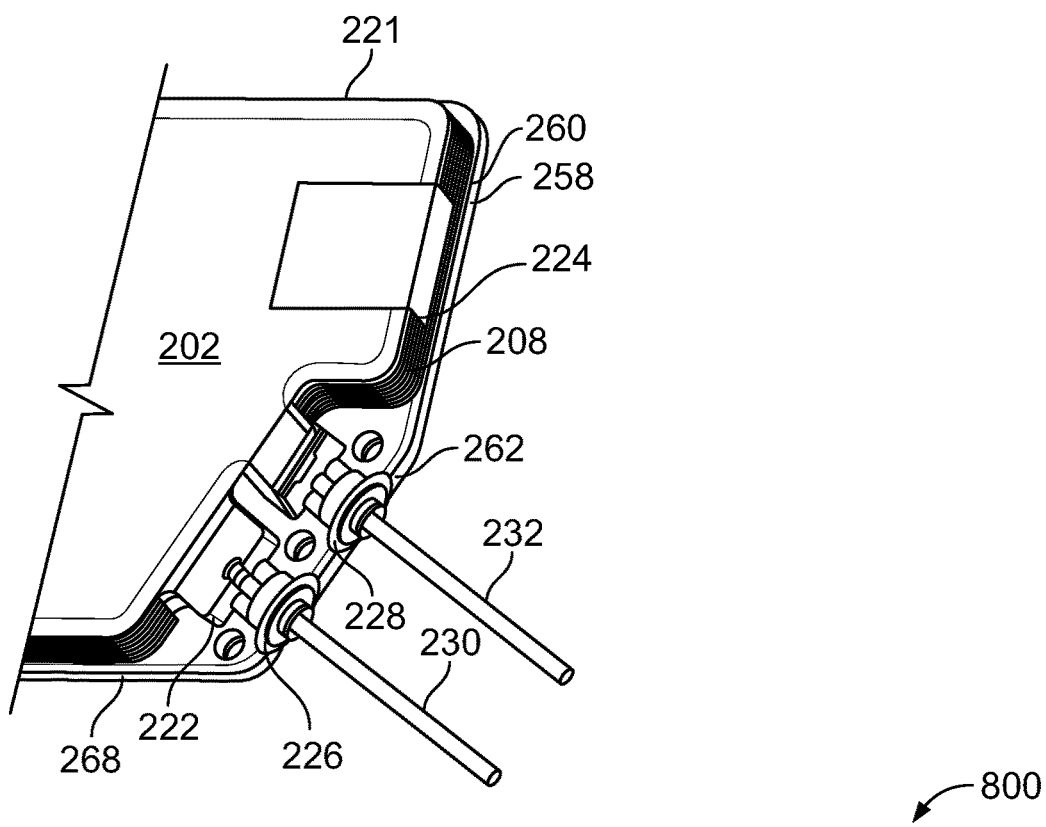
FIG. 7 illustrates a cut away perspective view of a capacitor, in accordance with embodiments herein.

As also illustrated in FIG. 5, an auxiliary tape 251 can be placed around the capacitor stack 202 to simplify the design of the case. In one example, the auxiliary tape 251 includes a stainless steel backing band with an adhesive connection to the second cover portion 208. In this manner, tolerance issues can be addressed with the auxiliary tape 251. As a result, a lower cost for the second cover portion 208 is provided. In addition, because of the simple geometries, and auxiliary tape 251, progressive dies can be utilized for forming the second cover portion 206, providing ease of manufacturing. The auxiliary tape 251 also provides a back up band to prevent laser heat during a welding manufacturing process from engaging and/or damaging the second cover portion 206.

With reference back to FIG. 2, the second cover portion 208, similar to the first cover portion 206, includes a plural recesses 252 that align with the adhesive tape 217 that bundles the capacitor stack 202. In one example, the second cover portion 208 is considered an exoskeleton of the capacitor. The second cover portion 208 has a second cover portion periphery 254 that similar to the first cover portion 206 that includes a front 256 that arcuately transitions to an input side 258 that includes a first portion 260 and a second portion 262 angled from the first portion 260, and having an opening 264 (FIG. 3) therein configured to receive ferrules of the capacitor stack 202. The input side 258 only has the simple geometry of the first portion 260 angled to the second portion 262 with no complex geometries. To this end, the input side 258 also arcuately transitions to a back 268 of the second cover portion periphery 254. The arcuate transition between the front 256 and input side 258, along with the arcuate transition between the input side 258 and back 268 have radii that again provide simple geometries. The back 268 extends to another arcuate transition to an arcuate side 270. The arcuate side 270 is generally arcuate, curving to another arcuate transition with the front 256. The second cover portion 208 along the front 256, back 268, input side 258, or arcuate side may include fastener bodies 246 that are of size and shape to accommodate the capacitor stack, and receive fasteners to couple to the second cover portion, and secure the first cover portion 206 to the second cover portion 208 with the capacitor stack disposed therein. The fastener bodies 272 may include cavities, indentations, openings, or the like to accommodate the coupling of the first cover portion 206 and second cover portion 208. Specifically, the first cover portion periphery 236 and the second cover portion periphery 254 align with the capacitor stack periphery 221 such that the first cover portion 206 and second cover portion 208 form a shell body 204 for encasing the capacitor stack 202 therein.

The second cover portion 208 in one example is a stainless steel case. The shape, tolerances, and geometry of the second cover portion 208 allows for a progressive die for case creation, improving the manufacturing process. Specifically, the higher tolerances allow for lower cost case design, as simpler geometries are achieved. The simple geometries also promote automation, and facilitate welding processes. As a result, the ease of manufacturing is enhanced, vastly improving over current manufacturing methodologies.

Figure 3:
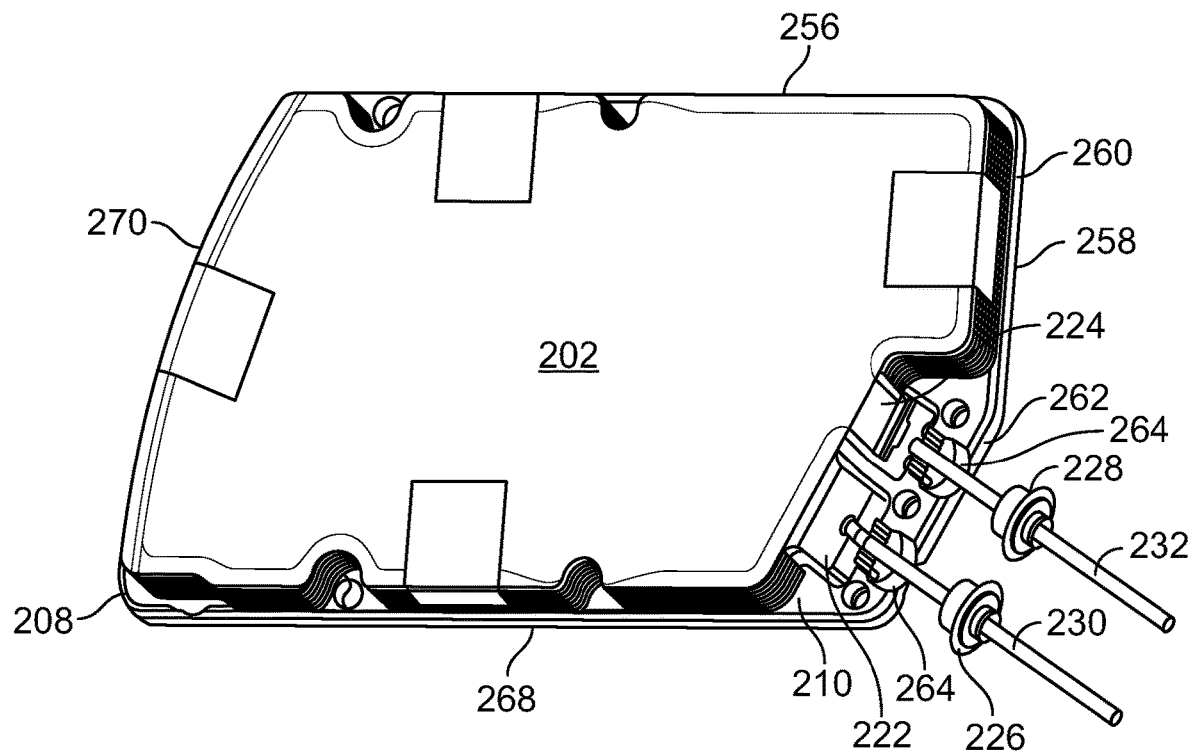
FIG. 3 illustrates a cut away perspective view of a capacitor, in accordance with embodiments herein.
Figure 4:
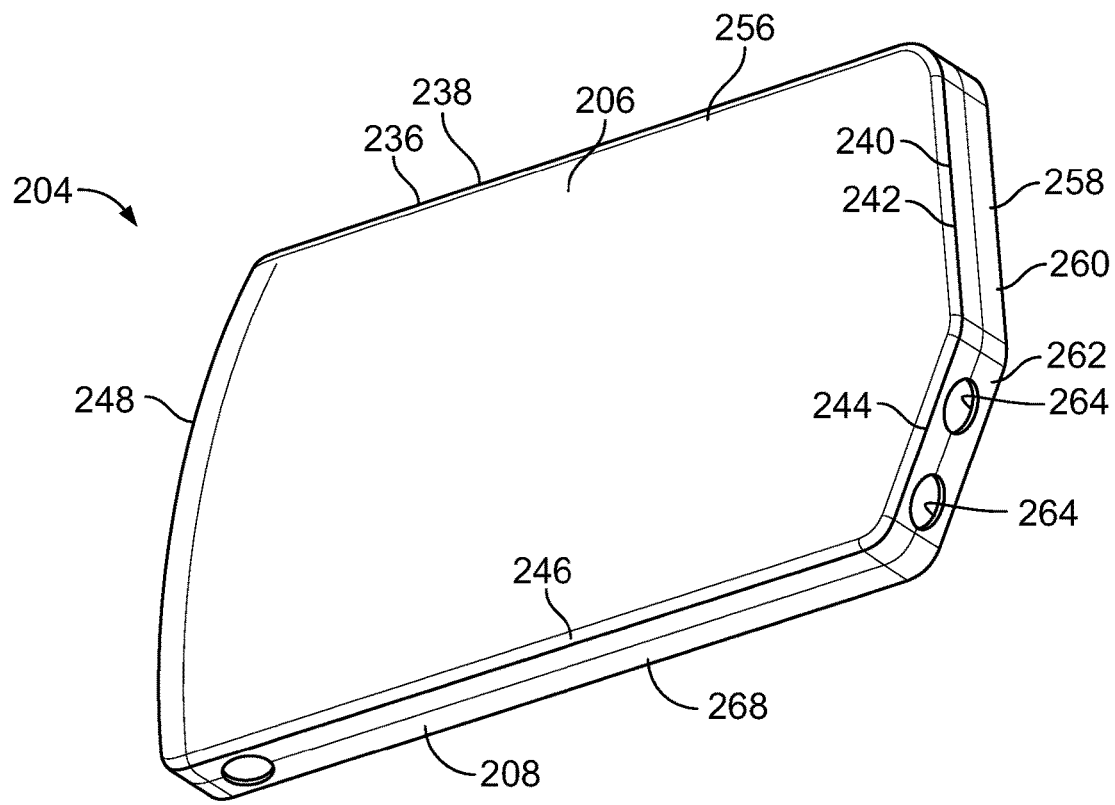
FIG. 4 illustrates a perspective view of a capacitor, in accordance with embodiments herein.

The first cover portion 206, and second cover portion 208 are of similar size and shape such that the first cover portion 206 matingly receives the second cover portion 208 to form the shell body 204 that protects the capacitor stack 202. In one example, the shell body 204 is a clam shell body (FIG. 3). In addition, because of the simple geometries the first cover portion 206 be manufactured using an injection molding process as an injection molded boot. This injection molded boot can then be received by the second cover portion 208 that can be a stainless steel casing. In this manner, compared to previous manufacturing techniques, the injection molding process is easy to replicate, no customization is required, and the number of shell bodies that can be manufactured per hour is greatly increased. As a result, a better, less expensive manufacturing process is provided. Specifically, with the anode taking up lest spatial requirements, the geometries of the first cover portion 206 and second cover portion 208 can be simplified, resulting in an improved manufacturing process.

For example, the simplification of the anode layers 212, cathode layers 214, and electrolytic layer 216 improves the quality of the capacitor stack 202. As illustrated in FIG. 5, increases radii for corners or transitions of the capacitor stack 202 allows for alignment of each layer 212, 214, 216 of the capacitor stack 202. Specifically, the outside edge, or periphery, of each layer 212, 214, 216 align to form the capacitor stack 221, eliminating the need for cathode tabs that have to bend for proper alignment. Such elimination of the cathode tabs lends to automation of the stacking process, thus improving manufacturing of the capacitor stack 202. The increased radii for transitions of the periphery of the anode layers 212, cathode layers 214, and electrolytic layer 216 also results in decreased cracking of each layer, including decreased anode cracking that can lead to lower yield. Consequently, yield is increased, and the life of the capacitor increased because of the simplified spatial design.

In addition, utilizing a first cover portion 206 that can be an injection molded boot cover around the capacitor stack 202 compared to the use of PEEK thin pockets presents numerous advantages. For example, the thicker boot cover allows for higher voltage withstand compared to a PEEK pocket. In addition, the thicker plastic material of such a boot allows for injection molding, presenting a more cost effective, simpler manufacturing process. In addition, the thick material also prevents electrical shorts, resulting in a more reliable capacitor. In addition, the amount of edge taping that is typically performed in a manual labor step is decreased, again, making for a faster and more time effective manufacturing process. In addition, such manufacturing is conducive to automation, again improving upon the manufacturing process.

Figure 8:
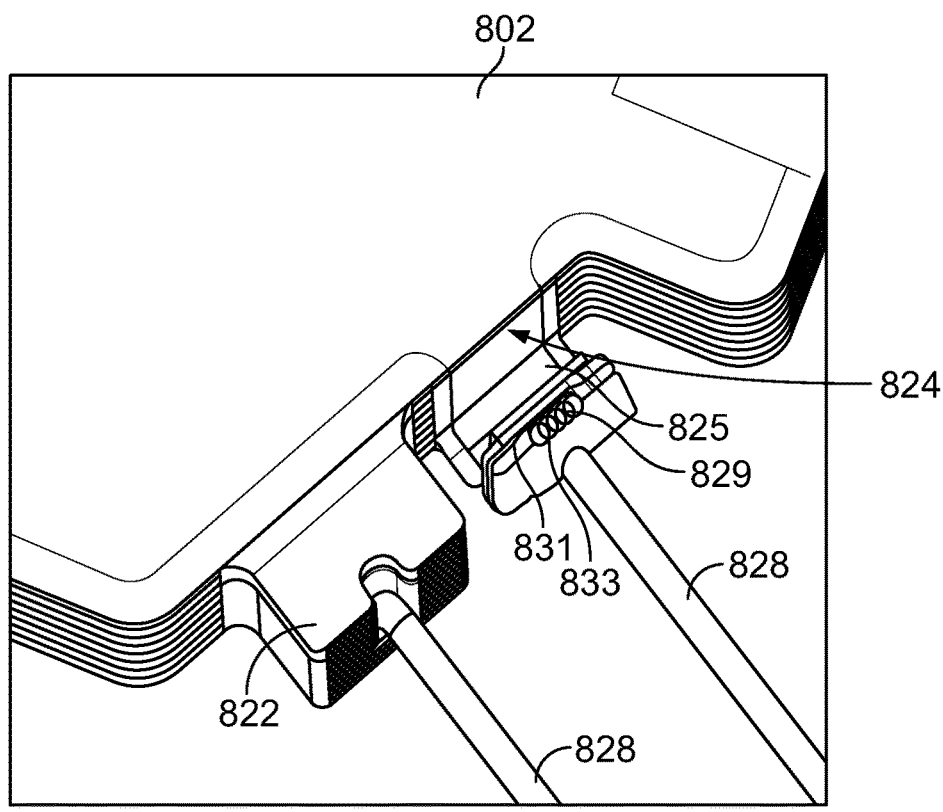
FIG. 8 illustrates a cut away perspective view of a capacitor, in accordance with embodiments herein.

FIG. 8 illustrates an alternative embodiment of a capacitor 800. In one example, the capacitor 800 of FIG. 8 is the capacitor of FIGS. 2-7. In particular, the capacitor is a high voltage capacitor can have an operating voltage of between 350-475 Volts and specifically between 400-465 Volts. In one example, the capacitor 800 is utilized in an IMD, including in an implantable cardioverter defibrillator (ICD).

The capacitor 800 includes a capacitor stack 802 as described in relation to FIGS. 2-7. The capacitor stack 802 includes a compressed anode portion 822 and compressed cathode portion 824 that present the input and output of the capacitor. The compressed anode portion 822 and compressed cathode portion 824 in one example are each welded together at an end of the capacitor stack 802 such that neither the compressed anode portion 822, nor the compressed cathode portion 824 engage a shell body (not shown).

In this embodiment, the compressed cathode portion 824 is resistance welded into a single stack, layer, or flat 825. In one example, the compressed cathode portion 824 is a titanium material. The compressed cathode portion 824 is coupled to a ferrule 828 via a wire assembly 829 to provide for a negative connection disposed outside of the shell body. In one example, the wire assembly 829 includes low resistance aluminum wire material to reduce internal resistance within the capacitor 800. The wire assembly 829 can include a flat wire adapter 831 coupled to a wire coil 833, or round wire. In one example, the flat wire adapter 831 is comprised of a titanium material, while the wire coil 833 comprises the aluminum material to provide the electrical coupling.

Figure 9:
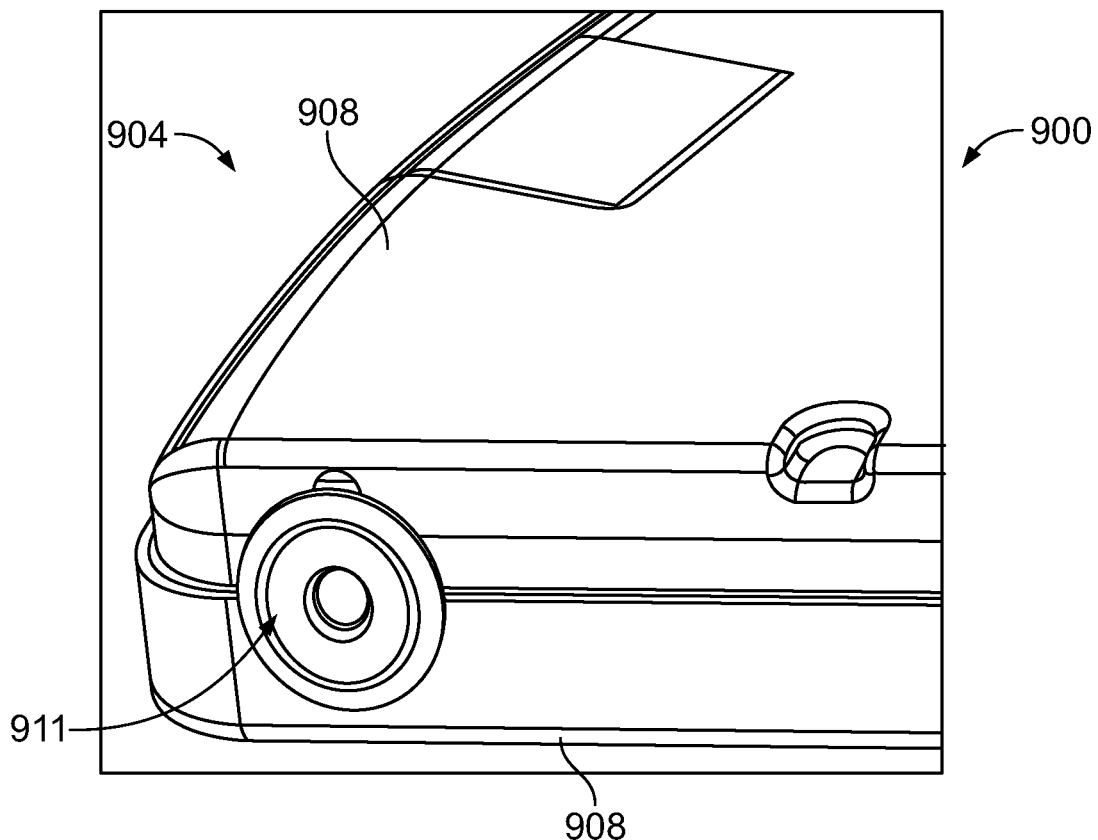
FIG. 9 illustrates a perspective view of a capacitor, in accordance with embodiments herein.
Figure 10:
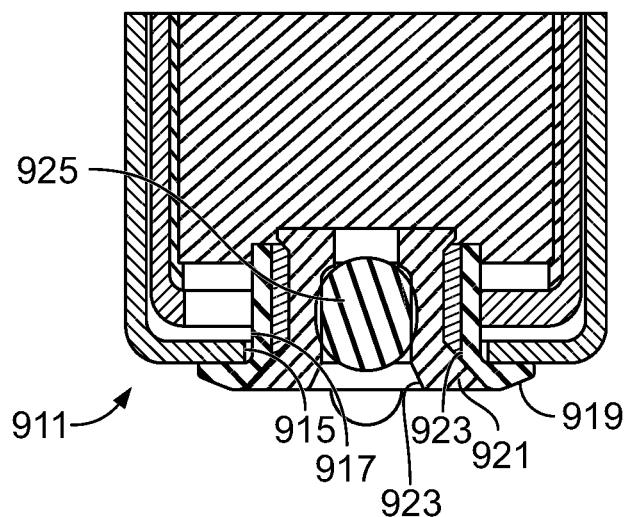
FIG. 10 illustrates a sectional view of a capacitor, in accordance with embodiments herein.

FIGS. 9-10 illustrate views of a capacitor 900, that in one example is the capacitor of FIGS. 2-7. In one example, the capacitor 900 is a high voltage capacitor can have an operating voltage of between 350-475 Volts and specifically between 400-465 Volts. In one example, the capacitor 900 is utilized in an IMD, including in an implantable cardioverter defibrillator (ICD).

The capacitor 900 includes a capacitor stack (not shown) that is protected, and covered by a shell body 904 that includes a first cover portion 906 and a second cover portion 908 that mechanically couple to one another and define a cavity that receives a capacitor stack. In one example, the first cover portion 906 may be made of a plastic material, and represent a plastic boot, while the second cover portion 908 is made of a stainless steel material that is considered a stainless steel case that functions to protect the capacitor stack 902.

Disposed within the first cover portion 906 and second cover portion 908 is a seal plug assembly 911 that include a plug 913. The plug in one example is press fit into the first cover portion 906 and/or second cover portion 908 during a welding process. In this manner, the shell 904 is sealed to contaminants after formation.

FIG. 10 illustrates one example of how the seal plug assembly 911 may be sealed. As illustrated, a first opening 915 is provided in the first cover portion 906, and a second opening 917 is provided in the second cover portion 908 that is encased by the first cover portion 906. In one example, the first cover portion 906 is made of a stainless steel material, while the second cover portion 908 is made of a plastic material.

A first insert 919 is disposed through the first opening 915, second opening 917, and within a capacitor stack 902. In one example, the first insert 919 is a stainless steel welded insert. In addition, a second insert 921 is disposed through the first opening 915 and second 917 adjacent the first insert 919, and having a third opening 923 disposed therethrough. In one example, the second insert 921 is press in molded and trimmed, and made of a plastic material. Disposed within the third opening 923 is a ball element 925, that in one example is a stainless steel seal ball. The ball element 925 seals the third opening 923 such that the first insert 919, second insert 921, and ball element seal the interior of the shell from contaminants. The ball element 925 functions as a low cost seal that avoids the need for a more expensive and complex laser welding operation, reducing manufacturing cost and time.

FIGS. 11A and 11B illustrate an injection molding devices 1100A, 1100B utilized to feed through the shell body and provide an anode and cathode wire seal without a parting line in the sealing surfaces. The injection molding devices 1100A, 1100B include a molding body 1102A, 1102B that in one example is made of a rubber material and feed through an insert. To this end, the molding body 1102A, 1102B includes an outer sealing surface 1104A, 1104B and an inner sealing surface 1106A, 1106B where the inner sealing surface defines an injection conduit 1108A, 1108B. In one example, as illustrated in FIG. 11A, the injection conduit 1108A has a constant diameter, whereas as illustrated in FIG. 11B, the injection conduit 1108B includes numerous sections 1110B, 1112B, 1114B that taper. In each instance, the wire seal is provided without a parting line, improving the performance of the capacitor by eliminating internal resistances that can cause inefficiencies, and excess heat that can also damage the capacitor. In addition, enhanced reliability of the sealing surface decreases electrolyte leaks during manufacturing and use.

FIG. 12 illustrates a capacitor assembly 1200 formed from first capacitor 1202, and a second capacitor 1204 stacked on one another to form a signal capacitor. The first capacitor 1202, and second capacitor 1204 may each be any of the capacitors presented in FIGS. 2-7. In particular, because each capacitor 1202, 1204 is formed utilizing an etching technique utilizing molybdic acid, a first cover portion 1206 that can be a boot, and a second cover portion 1208 that can be a case, can be reproduced to be the identical size and stackable on top of one another. When stacked on top of one another, ferrules 1207 of the first capacitor 1202, and ferrules 1207, 1209 of the second capacitor 1204 are coupled via a backing plate 1210 to an electronic coupler 1212. The capacitor assembly 1200 in one example operates in range between 700 Volts and 950 Volts, and more specifically between 800 Volts and 925 Volts.

The backing plate 1210 in one example is made from a plastic material. The backing plate 1210 is also configured to engage ferrule support structures 1213, 1215 of the first capacitor 1202 and second capacitor 1204 respectfully. In one example, each ferrule support structure 1213, 1215 is comprised of rubber material, and function as rubber stops of each capacitor 1202, 1204 that engage the backing plate 1210.

Regarding the coupling of the ferrules 1207, 1209 to the backing plate 1210, one ferrule 1207 of the first capacitor 1202 is coupled to a first anode, and one ferrule 1209 of the second capacitor 1204 is coupled to a second anode. Similarly, one ferrule 1207 of the first capacitor is coupled to a first cathode, and one ferrule 1209 of the second capacitor 1204 is coupled to a second cathode. Each ferrule 1207, 1209 of each capacitor 1202, 1204 couples to the backing plate 1210 to provide a combined anode ferrule 1214 and a combined cathode ferrule 1216. The combined anode ferrule 1214 and combined cathode ferrule 1216 electrically couple into the electronic coupler 1212 along with a high voltage add-on wire 1226. The electronic coupler 1212 includes plural pin elements 1218 that mechanically couple the electronic coupler 1212 to a substrate such as a circuit board, printed circuit board, or the like that electrically couples electronic components.

Figure 13:
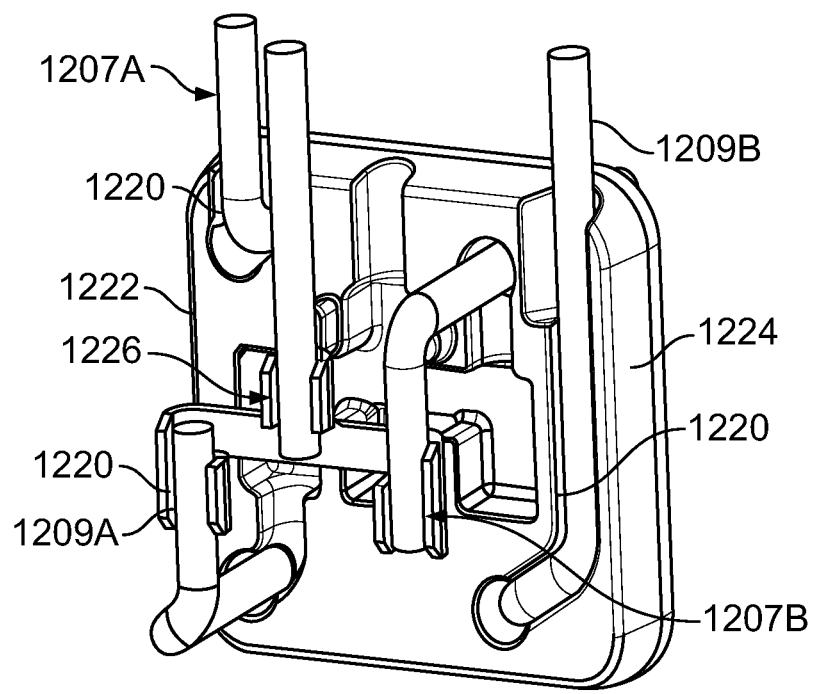
FIG. 13 illustrates a perspective view of backing plate, in accordance with embodiments herein.

FIG. 13 illustrates a cutaway perspective view of the backing plate 1210 to show how the individual ferrules 1207A, 1207B, 1209A, 1209B of each capacitor 1202, 1204 are received and coupled to the electronic coupler 1212. As illustrated, the backing plate 1210 includes indentations or grooves 1220 for receiving each ferrule 1207A, 1207B, 1209A, 1209B of the first capacitor 1202 and second capacitor 1204. As illustrated, the positive ferrule 1207A of the first capacitor 1202 is coupled to the cathode of the capacitor stack of the first capacitor 1202 and is coupled on a first side 1222 of the backing plate 1210, while the negative ferrule 1207B of the first capacitor 1202 is coupled to the anode of the capacitor stack of the first capacitor 1202 and is coupled on a second side 1224 of the backing plate 1210. In particular, the positive ferrule 1207A of the first capacitor 1202 in one example is welded to the backing plate 1210.

Meanwhile, the positive ferrule 1209A of the second capacitor 1204 is coupled to the cathode of the capacitor stack of the second capacitor 1204 and is coupled on the first side 1222 of the backing plate 1210, wherein the negative ferrule 1209B of the second capacitor 1204 is coupled to the anode of the capacitor stack of the second capacitor 1204, and is coupled on the second side 1224 of the backing plate 1210. In particular, in one example, the negative ferrule 1209B of the second capacitor 1204 is welded to the backing plate 1210.

In addition, a high voltage add-on wire 1226 is also welded to the backing plate 1210. In this manner, the backing plate 1210 allows for the positive, negative, and high voltage wire to be welded at the same manufacturing step. As a result, ease of manufacturing is realized for the welding operation.

Figure 14:
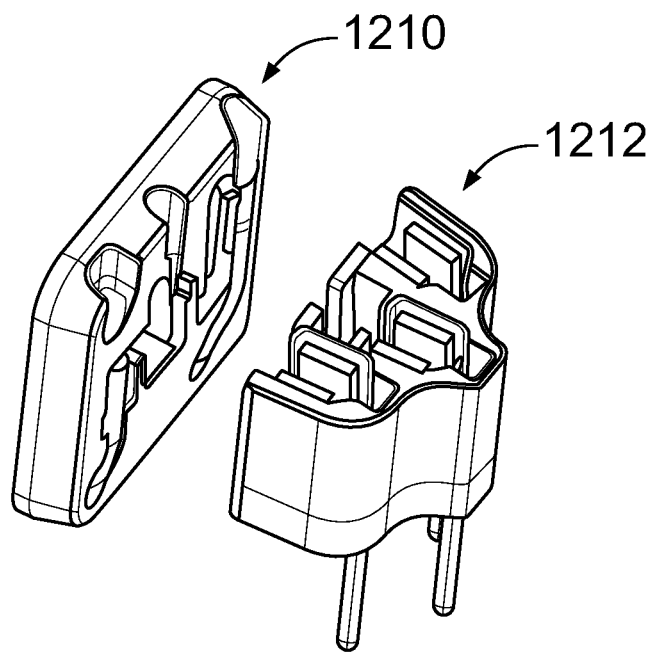
FIG. 14 illustrates a perspective view of backing plate and electronic coupler, in accordance with embodiments herein.

FIGS. 14-16 illustrate views of the backing plate 1210 and electronic coupler 1212 to illustrate how the backing plate 1210 and electronic coupler 1212 attach to one another. Specifically, the backing plate 1210 in one example includes post elements 1228 that align with openings within the electronic coupler 1212, while the electronic coupler 1212, includes a post element 1230 that aligns with and is received in an opening within the backing plate 1210. In one example, the post elements 1228 of the backing plate 1210, and post element 1230 of the electronic coupler 1212 are each made of a plastic material. Each of the posts 1228, 1230 ensure the backing plate 1210 and electronic coupler 1212 are aligned. By ensuring the alignment, a mechanical coupling of the backing plate 1210 and electronic coupler 1212 is provided such that electrical coupling between the first capacitor and second capacitor to the pin elements 1218 of the electronic coupler 1212 is also presented. In particular, the electronic coupler 1212 includes a housing 1232 that defines a first cavity 1234 for receiving a positive input, a second cavity 1236 for receiving a high voltage input, and a third cavity 1238 for receiving a negative input from the backing plate 1210. Each cavity may include additional structure, including nut elements, arcuate walls, or the like that direct the positive input, high voltage input, and negative input to mechanically and electrically couple to the pin elements 1218.

Figure 17:
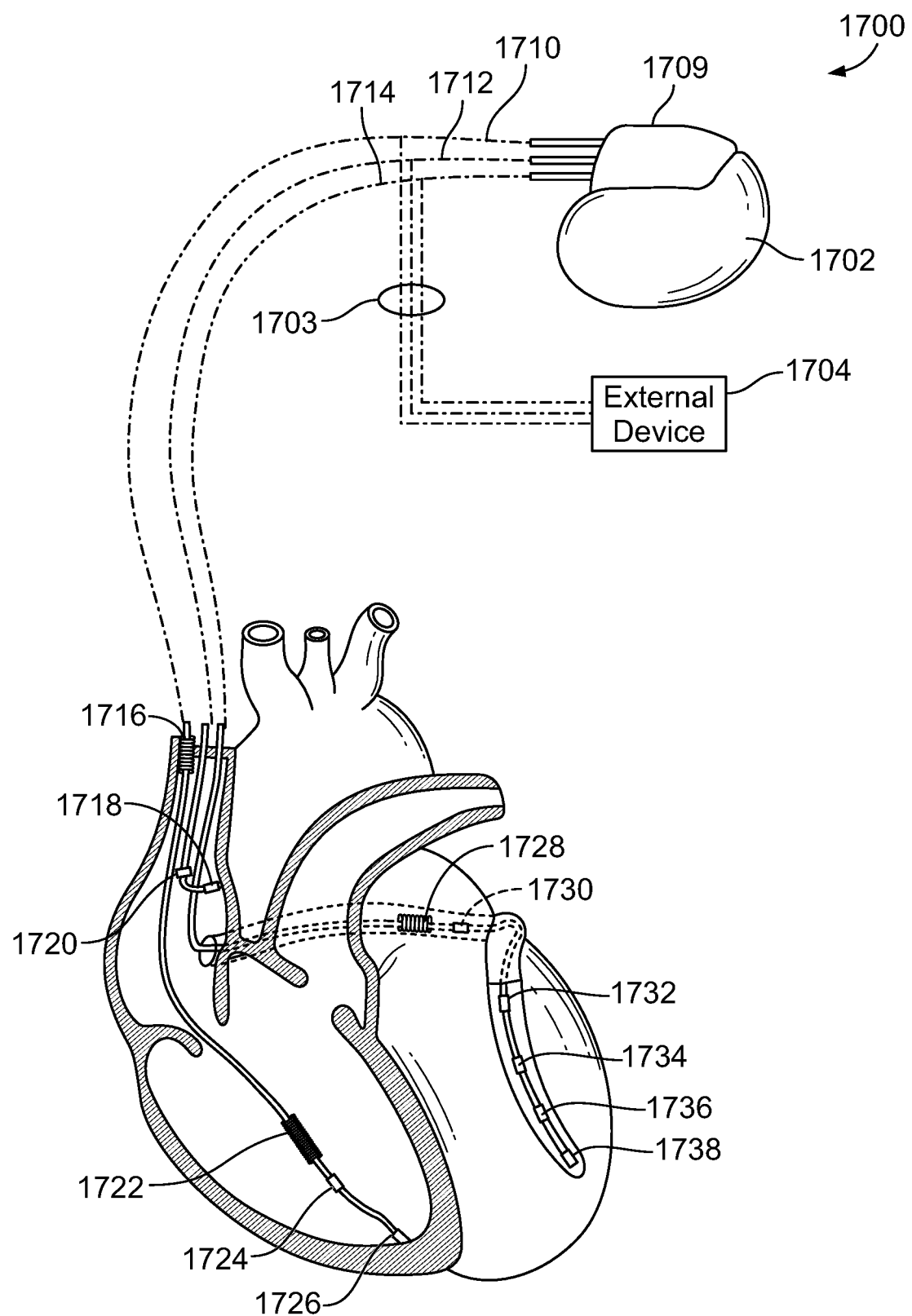
FIG. 17 illustrates a schematic diagram of an IMD in accordance with embodiments herein.

FIG. 17 illustrates an IMD 1700 that in one example is a dual-chamber stimulation device capable of treating both fast and slow arrhythmias with stimulation therapy, including cardioversion, defibrillation, anti-tachycardia pacing and pacing stimulation, as well as capable of detecting heart failure, evaluating its severity, tracking the progression thereof, and controlling the delivery of therapy and warnings in response thereto. The IMD 1700 may be controlled to sense atrial and ventricular waveforms of interest, discriminate between two or more ventricular waveforms of interest, deliver stimulus pulses or shocks, and inhibit application of a stimulation pulse to a heart based on the discrimination between the waveforms of interest and the like. Exemplary structures for the IMD 1700 are discussed and illustrated in the drawings herewith.

The IMD 1700 includes a housing 1702 that is joined to a header assembly 1709 that holds receptacle connectors connected to a right ventricular lead 1710, a right atrial lead 1712, and a coronary sinus lead 1714, respectively. The leads 1712, 1714 and 1710 measure cardiac signals of the heart. The right atrial lead 1712 includes an atrial tip electrode 1718 and an atrial ring electrode 1720. The coronary sinus lead 1714 includes a left atrial ring electrode 1728, a left atrial coil electrode 1730 and one or more left ventricular electrodes 1732-1738 (e.g., also referred to as P1, M1, M2 and D1) to form a multi-pole LV electrode combination. The right ventricular lead 1710 includes an RV tip electrode 1726, an RV ring electrode 1724, an RV coil electrode 1722, and an SVC coil electrode 1716. The leads 1712, 1714 and 1710 detect IEGM signals that are processed and analyzed as described herein. The leads 1712, 1714 and 1710 also delivery therapies as described herein.

During implantation, an external device 1704 is connected to one or more of the leads 1712, 1714 and 1710 through temporary inputs 1703. The inputs 1703 of the external device 1704 receive IEGM signals from the leads 1712, 1714 and 1710 during implantation and display the IEGM signals to the physician on a display. Hence, the external device 1704 receives the IEGM cardiac signals through telemetry circuit inputs. The physician or another user controls operation of the external device 1704 through a user interface. While the example embodiment of FIG. 17 illustrates an IMD 1700 that includes leads, such embodiment is for exemplary purposes only, in other example embodiments, the IMD may be a leadless IMD.

Figure 18:
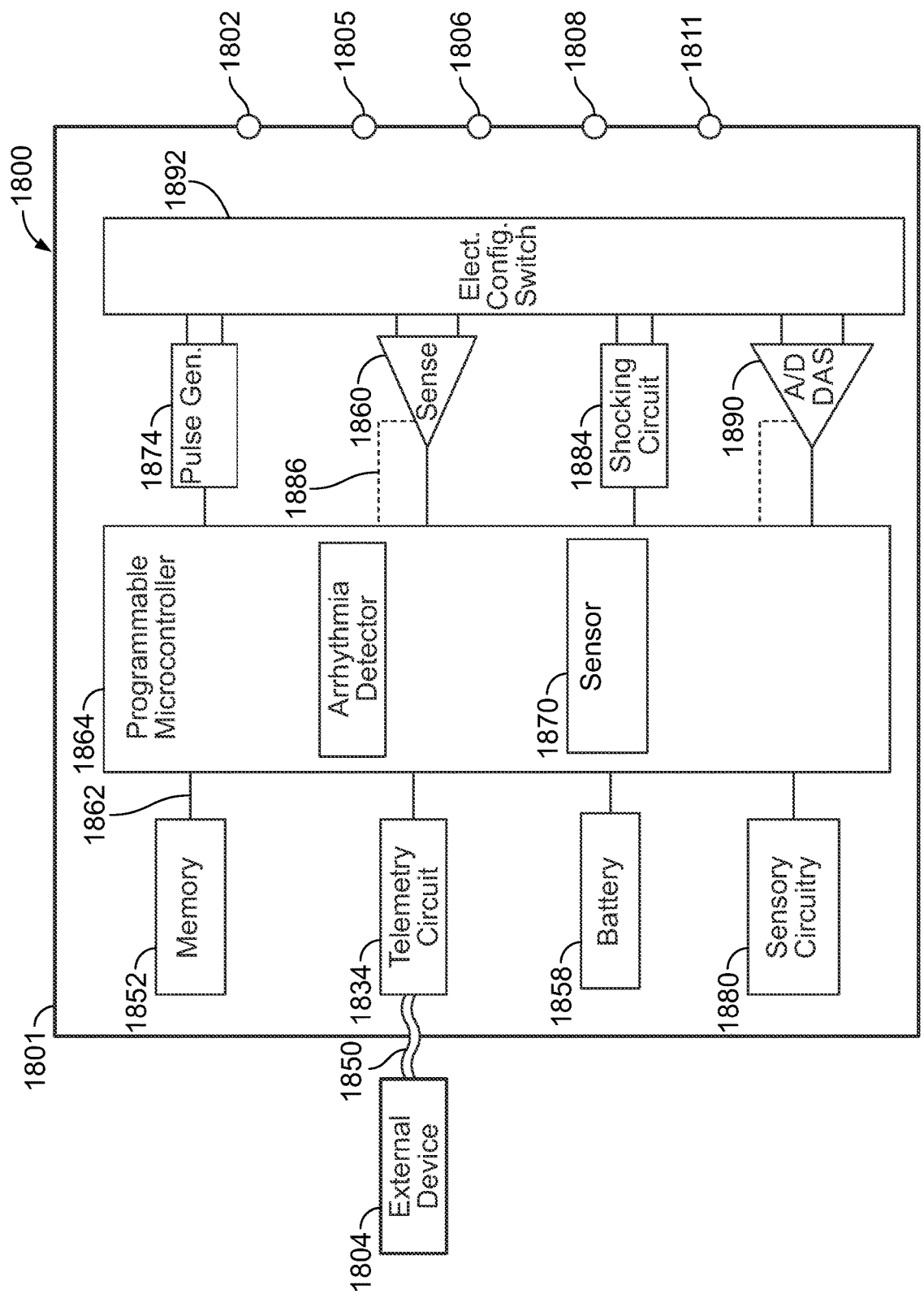
FIG. 18 illustrates a schematic block diagram of an IMD in accordance with embodiments herein.

FIG. 18 illustrates an example block diagram of a IMD 1800 that is implanted into the patient as part of the implantable cardiac system. The IMD 1800 may be implemented as a full-function biventricular pacemaker, equipped with both atrial and ventricular sensing and pacing circuitry for four chamber sensing and stimulation therapy (including both pacing and shock treatment). Optionally, the IMD 1800 may provide full-function cardiac resynchronization therapy. Alternatively, the IMD 1800 may be implemented with a reduced set of functions and components. For instance, the monitoring device may be implemented without ventricular sensing and pacing.

The IMD 1800 has a housing 1801 to hold the electronic/computing components. The housing 1801 (which is often referred to as the "can", "case", "encasing", or "case electrode") may be programmably selected to act as the return electrode for certain stimulus modes. Housing 1801 further includes a connector (not shown) with a plurality of terminals 1802, 1805, 1806, 1808, and 1811. The type and location of each electrode may vary. For example, the electrodes may include various combinations of ring, tip, coil and shocking electrodes and the like.

The IMD 1800 also includes a telemetry circuit 1834 that as a primary function allows intracardiac electrograms and status information relating to the operation of the IMD 1800 (as contained in the microcontroller 1864 or memory 1852) to be sent to the external device 1804 through the established communication link 1850.

The programmable microcontroller 1864 controls various operations of the IMD 1800. Microcontroller 1864 includes a microprocessor (or equivalent control circuitry), RAM and/or ROM memory, logic and timing circuitry, state machine circuitry, and I/O circuitry. The IMD 1800 further includes a first chamber pulse generator 1874 that generates stimulation pulses for delivery by one or more electrodes coupled thereto. The pulse generator 1874 is controlled by the microcontroller 1864 via control signal 1876. The pulse generator 1874 is coupled to the select electrode(s) via an electrode configuration switch 1892, which includes multiple switches for connecting the desired electrodes to the appropriate I/O circuits, thereby facilitating electrode programmability. The switch 1892 is controlled by a control signal from the microcontroller 1864.

Microcontroller 1864 is illustrated to include timing control circuitry 1866 to control the timing of the stimulation pulses (e.g., pacing rate, atrio-ventricular (AV) delay, atrial interconduction (A-A) delay, or ventricular interconduction (V-V) delay, etc.). Microcontroller 1864 also has an arrhythmia detector 1868 for detecting arrhythmia conditions. Although not shown, the microcontroller 1864 may further include other dedicated circuitry and/or firmware/software components that assist in monitoring various conditions of the patient's heart and managing pacing therapies.

The IMD 1800 also includes one or more sensors 1870. The one or more sensors 1870 can include physiological sensors that detect characteristics associated with the heart of the patient. Alternatively, the one or more sensors 1870 can be environmental sensors that detect characteristics associated with the environment of the patient.

The IMD 1800 is further equipped with a communication modem (modulator/demodulator) to enable wireless communication with other devices, implanted devices, and/or external devices. The IMD 1800 includes sensing circuitry 1880 selectively coupled to one or more electrodes that perform sensing operations, through the switch 1892, to detect the presence of cardiac activity.

The output of the sensing circuitry 1880 is connected to the microcontroller 1864 which, in turn, triggers or inhibits the pulse generator 1874 in response to the absence or presence of cardiac activity. The sensing circuitry 1880 receives a control signal 1878 from the microcontroller 1864 for purposes of controlling the gain, threshold, polarization charge removal circuitry (not shown), and the timing of any blocking circuitry (not shown) coupled to the inputs of the sensing circuitry.

In the example of FIG. 18, a single sensing circuit 1880 is illustrated. Optionally, the IMD 1800 may include multiple sensing circuit, similar to sensing circuitry 1880, where each sensing circuit is coupled to one or more electrodes and controlled by the microcontroller 1864 to sense electrical activity detected at the corresponding one or more electrodes. The sensing circuitry 1880 may operate in a unipolar sensing configuration or in a bipolar sensing configuration. The IMD 1800 further includes an analog-to-digital (ND) data acquisition system (DAS) 1890 coupled to one or more electrodes via the switch 1892 to sample cardiac signals across any pair of desired electrodes.

The microcontroller 1864 is also coupled to a memory 1852 by a suitable data/address bus 1862. The programmable operating parameters used by the microcontroller 1864 are stored in memory 1852 and used to customize the operation of the IMD 1800 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart within each respective tier of therapy.

A battery 1858 provides operating power to all of the components in the IMD 1800. The IMD 1800 further includes an impedance measuring circuit 1860, which can be used for many things, including: lead impedance surveillance during the acute and chronic phases for proper lead positioning or dislodgement; detecting operable electrodes and automatically switching to an operable pair if dislodgement occurs; measuring thoracic impedance for determining shock thresholds; detecting when the device has been implanted; measuring stroke volume; and detecting the opening of heart valves; and so forth. The impedance measuring circuit 1860 is coupled to the switch 1892 so that any desired electrode may be used. The IMD 1800 can be operated as an implantable cardioverter/defibrillator (ICD) device, which detects the occurrence of an arrhythmia and automatically applies an appropriate electrical shock therapy to the heart aimed at terminating the detected arrhythmia. To this end, the microcontroller 1864 further controls a shocking circuit 1884 by way of a control signal 1886.

Closing

It should be clearly understood that the various arrangements and processes broadly described and illustrated with respect to the Figures, and/or one or more individual components of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method, or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the figures, which illustrate example methods, devices, and program products according to various example embodiments. The program instructions may be provided to a processor of a general-purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally, or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A capacitor for an implanted medical device, comprising:
   a capacitor stack including an anode layer, cathode layer, and electrolytic layer electrically coupled together, the capacitor stack including a capacitor stack periphery;
   a first cover portion having a first cover portion periphery that aligns with the capacitor stack periphery; and
   a metal case having a second cover portion periphery that aligns with the capacitor stack periphery and receives the first cover portion periphery to form a shell body for encasing the capacitor stack therein;
   wherein the capacitor stack includes a compressed anode portion and a compressed cathode portion that are coupled together at an end of the capacitor stack without the compressed anode portion or the compressed cathode portion engaging the first cover portion or the metal case such that the capacitor stack is isolated from the metal case to provide a neutrally charged metal case that is electrically coupled within the implanted medical device.

2. The capacitor of claim 1, wherein the first cover portion comprises an injection molded plastic.

3. The capacitor of claim 1, wherein the metal case comprises stainless steel.

4. The capacitor of claim 1, wherein the capacitor stack includes a first ferrule that is coupled with the compressed anode portion and extends through the shell body, and a second ferrule that is coupled with the compressed anode portion and extends through the shell body.

5. The capacitor of claim 4, wherein the compressed cathode portion includes a flat that that is welded to a wire assembly.

6. The capacitor of claim 1, wherein the capacitor stack periphery includes a first front that arcuately transitions to first input side that includes a first portion and a second portion angled from the first portion, the first input side arcuately transitioning to a first back that arcuately transitions into a first arcuate side that arcuately transitions into the first front.

7. The capacitor of claim 6, wherein the first cover portion periphery includes a second front that arcuately transitions to a second input side that includes a third portion and a fourth portion angled from the third portion, the second input side arcuately transitioning to a second back that arcuately transitions into a second arcuate side that arcuately transitions into the second front of the first cover portion periphery; and the second cover portion periphery includes a third front that arcuately transitions to a third input side that includes a fifth portion and a sixth portion angled from the third portion, the third input side arcuately transitioning to a third back that arcuately transitions into third arcuate side that arcuately transitions into the third front of the second cover portion periphery.

8. A capacitor for an implanted medical device, the capacitor comprising:
   a capacitor stack including an anode layer, cathode layer, and electrolytic layer electrically coupled together, the capacitor stack including a capacitor stack periphery;
   a plastic cover portion having a first cover portion periphery that aligns with the capacitor stack periphery;
   a metal cover portion having a second cover portion periphery that aligns with the capacitor stack periphery and receives the first cover portion periphery to form a shell body for encasing the capacitor stack therein;
   wherein the capacitor stack includes a compressed anode portion and a compressed cathode portion that are coupled together at an end of the capacitor stack without the compressed anode portion or the compressed cathode portion engaging the plastic cover portion or the metal cover portion such that the capacitor stack is isolated from the metal cover portion to provide a neutrally charged metal cover portion that is electrically coupled within the implanted medical device.

9. The capacitor of claim 8, wherein the plastic cover portion comprises an injection molded plastic.

10. The capacitor of claim 8, wherein the metal cover portion comprises stainless steel.

11. The capacitor of claim 8, wherein the capacitor stack includes a first ferrule coupled with the compressed anode portion and that extends through the shell body, and a second ferrule coupled with the compressed cathode portion and that extends through the shell body.

12. The capacitor of claim 11, wherein the compressed cathode portion includes a flat that that is welded to a wire assembly.

13. The capacitor of claim 8, wherein the capacitor stack periphery includes a first front that arcuately transitions to a first input side that includes a first portion and a second portion angled from the first portion, and the input side arcuately transitions to a first back that arcuately transitions into a first arcuate side that arcuately transitions into the first front.

14. The capacitor of claim 13, wherein the first cover portion periphery includes a second front that arcuately transitions to a second input side that includes a third portion and a fourth portion angled from the third portion.

15. The capacitor of claim 14, wherein the second input side of the first cover periphery arcuately transitions to a second back that arcuately transitions into a second arcuate side that arcuately transitions into the second front of the first cover portion periphery.

16. The capacitor of claim 8, wherein the second cover portion periphery includes a front that arcuately transitions to an input side that includes a first portion and a second portion angled from the first portion.

17. The capacitor of claim 16, wherein the input side of the second cover portion periphery arcuately transitions to a back that arcuately transitions into an arcuate side that arcuately transitions into the front of the second cover portion periphery.

* * * * *